United States Patent [19]

Bower

[11] Patent Number: 5,299,574
[45] Date of Patent: Apr. 5, 1994

[54] METHOD AND APPARATUS FOR SELECTIVE CORONARY ARTERIOGRAPHY

[76] Inventor: P. Jeffery Bower, 199 Suave Rd., River Ridge, La. 70123

[21] Appl. No.: 901,833

[22] Filed: Aug. 29, 1986

[51] Int. Cl.⁵ .......................................... A61M 25/00
[52] U.S. Cl. .................................. 128/658; 604/280; 604/281
[58] Field of Search .................... 604/95, 280–284; 128/656–658

[56] References Cited

U.S. PATENT DOCUMENTS

| | | | |
|---|---|---|---|
| 3,935,857 | 2/1976 | Co | 604/281 |
| 4,033,331 | 7/1977 | Guss et al. | 604/281 |
| 4,117,836 | 10/1978 | Erikson | 604/281 |

OTHER PUBLICATIONS

Cordis Corporation, 149-1936 Rev 2, 1976 "A Ducor Coronary Bypass Angiographic Catheter," Miami, Fla.
Cordis Corporation, A149-1883 Rev O, 1973 "Introducing: A New Ducor Brachial-Coronary Angiographic Catheter".
Bourassa et al., "Selective Coronary Arteriography by the Percutaneous Femoral Artery Approach," *American Journal of Roentgenology, Radiation Therapy and Nuclear Medicine.* —vol. CVII No. 2, Oct. 1969.
Chermet et al. "Aortography with the Long Catheter Needle." *Radiology* (USA), vol. 134, No. 1 pp. 242–243, Jan. 1980.
Judkins, "Selective Coronary Arteriography" *Radiology*, vol. 89, No. 5, pp. 815–824, Nov., 1967.

*Primary Examiner*—Stephen C. Pellegrino
*Assistant Examiner*—Ralph A. Lewis
*Attorney, Agent, or Firm*—Keaty & Keaty

[57] ABSTRACT

A catheter for selective coronary arteriography has an elongated tubular member with an interior channel. The catheter includes a shank and a specifically configured end part curved in such a way so that a portion of it seats against a wall of the aorta and another portion is seated in a coronary cusp when the catheter is in place.

12 Claims, 2 Drawing Sheets

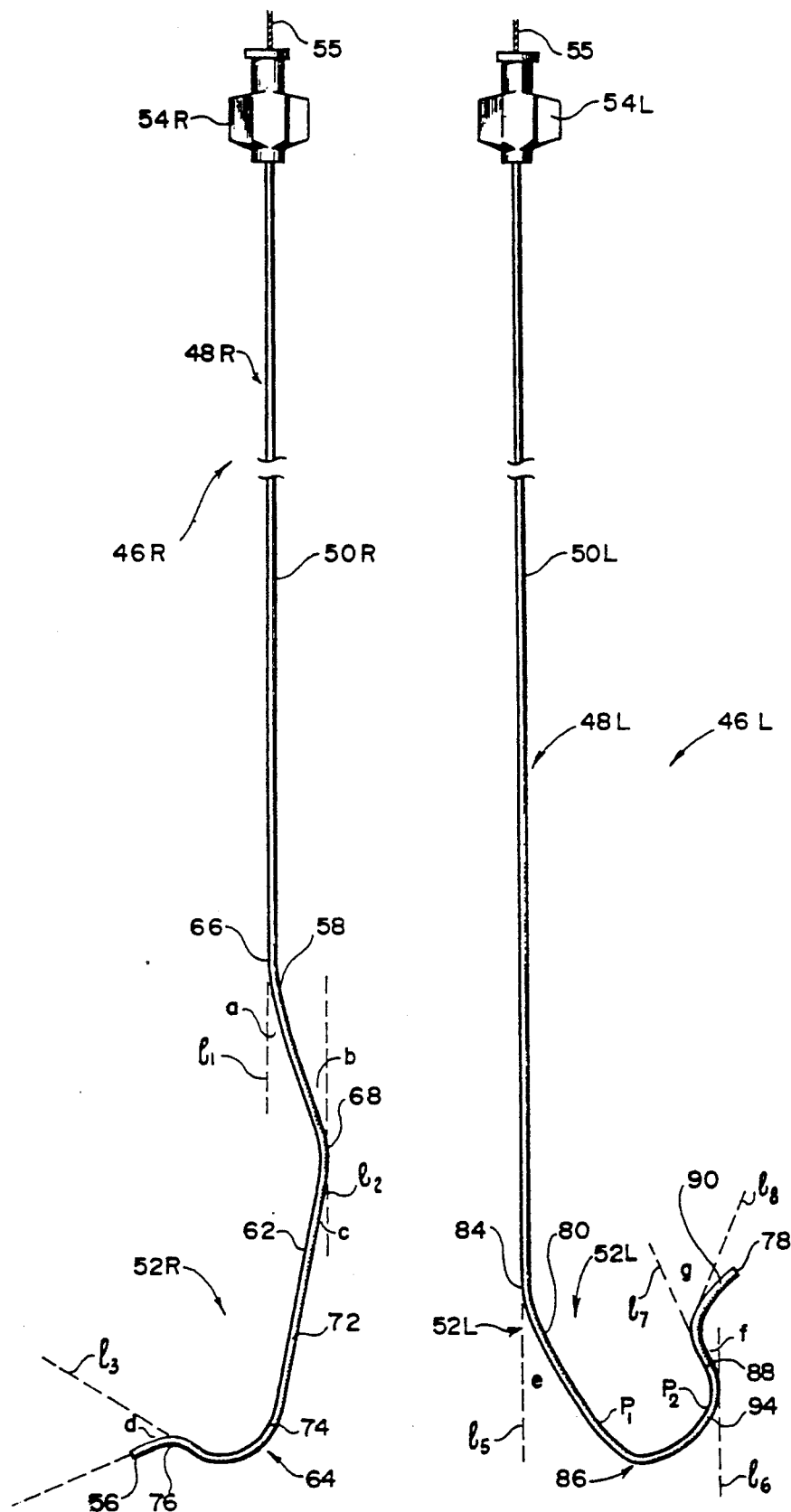

METHOD AND APPARATUS FOR SELECTIVE CORONARY ARTERIOGRAPHY

BACKGROUND OF THE INVENTION

1. Field of the Invention

This invention concerns a catheter for selective coronary arteriography of a coronary artery. More particularly, it concerns such a catheter which is inserted through an artery in the arm.

2. General Discussion of the Background

Many heart diseases are caused by occlusion of one or more of the coronary arteries that supply oxygen to the heart. The proper diagnosis and treatment of these diseases requires an accurate evaluation of the condition of the coronary arteries. One frequently used technique for making such a diagnosis is coronary arteriography, a procedure in which a catheter is inserted into the aorta of the heart and positioned adjacent or within the ostium of a coronary artery. A radiopaque dye is then injected through the catheter into the coronary artery while an X-ray is taken. The pattern of movement of the dye, which can be detected on a flouroscopic screen, helps provide an assessment of the condition of the artery being examined.

The catheters are inserted into the aorta either through the femoral artery adjacent the groin or through the brachial artery in the arm. The catheters shown in U.S. Pat. Nos 4,033,331, 4,117,836 and Canadian Patent No. 930636 are specifically configured for insertion through the femoral artery. There are several disadvantages, however, to this approach In the first place, femoral catheterization is suffiently traumatic that the patient's leg must remain flat for about four hours after the procedure to avoid bleeding. A secondary problem is that the surge of blood pressure within the femoral artery makes it difficult to control bleeding after the procedure.

Catheterization through the brachial artery in the arm avoids these problems. During the procedure and afterwards, the surge of arterial pressure can be more easily controlled by putting a pressure cuff around the upper arm. Subsequent to brachial catheterization, only about 1½ hours of rest are required since stresses on the arm are not great when the patient starts walking.

In spite of the advantages of brachial catheterization, there are no catheters which are specifically configured for insertion through the brachial artery for secure placement within the aorta. U.S. Pat. Nos. 3,935,857 and 4,531,936 disclose catheters which can be inserted into an artery in the arm or leg. The '857 catheter, however, is simply a continuous curve having a pair of legs disposed at an angle of about 85°. Such a configuration does not allow the catheter to be securely seated in the aorta with the open end of the catheter inserted into an ostium of the coronary artery which is being catheterized. The catheter is therefore relatively free to move about in the aorta, which can allow the tip to become dislodged from the arterial ostium. This problem can cause serious delays in arteriography which increase the duration of the procedure and the risk of side effects.

It is accordingly an object of this invention to provide a catheter which is specifically configured for insertion through an artery in the arm.

It is another object of the invention to provide such a catheter having an end portion which is shaped to seat firmly within the aorta such that the open tip of the catheter can be easily and securely placed in the ostium of the artery being examined.

It is a further object of the invention to provide such a catheter which is not easily dislodged once in place.

Even yet another object of the invention is to provide such a catheter which can minimize damage to the brachial, axillary and subclavian arteries through which it is inserted.

SUMMARY OF THE INVENTION

The aforementioned objects are achieved by providing a catheter for selective coronary arteriography in which the catheter comprises an elongated, tubular member having an interior channel extending the length of the catheter. The catheter includes a shank and an end part, the end part being curved so that a portion of it seats against a wall of the aorta and another portion is seated in a coronary cusp when the catheter is in place.

The end part defines an opening through which a radiopaque material is introduced into the coronary artery. The end part has an upwardly curved terminal portion that curves upwardly from the portion seated in the coronary cusp to a level adjacent an ostium of the coronary artery when the catheter is in place. In especially preferred embodiments, the terminal portion comprises an upwardly curved segment which seats within the coronary cusp and a downwardly curved segment which seats in the ostium.

The catheter can be specifically configured to examine the right coronary artery. Such a right coronary catheter has a shank long enough to extend through a right brachial, right axillary and right subclavian artery. The end part, which is configured to seat within the aorta, is substantially contained in one plane and is comprised of a first curved portion, second curved portion, and generally J-shaped terminal portion. The first and second portions are slightly curved in opposite directions, while the generally J-shaped portion includes a straight segment, a strongly upwardly curved segment for seating in the right coronary cusp, and a slightly downwardly curved segment for seating in the ostium of the right coronary artery.

In those embodiments of the catheter which are configured for catheterization of the left coronary artery, the catheter again comprises a shank and an end part. The shank is long enough to extend through the right brachial, right axillary and right subclavian artery to the aorta. The end part is contained in one plane and comprises, from the shank to a terminus of the end part, a slightly curved first portion for seating against a right side of the interior wall of the aorta, and a generally U-shaped terminal portion for seating in the left coronary cusp. An ascending segment of the U-shaped terminal portion extends upwardly to the ostium of the left coronary artery, the ascending segment comprising a first inclined segment slightly curved toward the shank and a second inclined segment slightly curved upwardly and away from the shank for seating in the ostium.

BRIEF DESCRIPTION OF THE DRAWINGS

Additional objects and advantages of the invention will be better understood by reference to the following drawings, in which:

FIG. 2 is a fragmentary plan view of the right coronary catheter, a portion of the shank being broken away.

FIG. 3 is a fragmentary plan view of the left coronary catheter, a portion of the shank being broken away.

DETAILED DESCRIPTION OF PREFERRED EMBODIMENT

Figure 1:
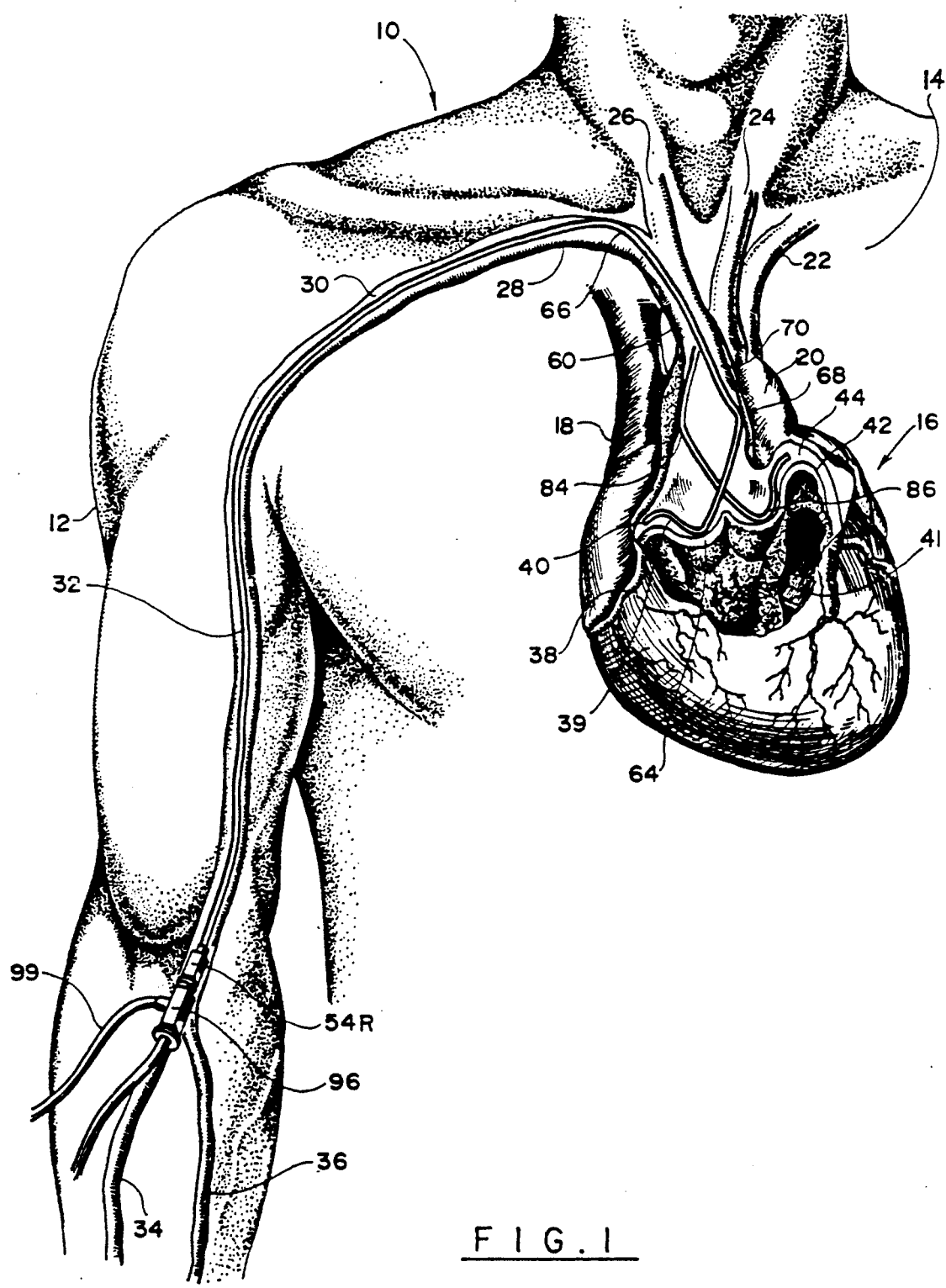
FIG. 1 is a schematic representation of an upper portion of the human body showing a heart with a right coronary catheter and a left coronary catheter therein, only a portion of the shank of the left coronary catheter being shown.

The following detailed description is being made in accordance with requirements of law that the inventor disclose the best mode known to him of making and using the invention. This description of a preferred embodiment is for purposes of illustration only, and is not intended to limit the scope of the invention which is more appropriately construed in accordance with the appended claims.

FIG. 1 shows the upper portion of a human body 10 having an arm 12 and thorax 14. Within the thorax is located heart 16, which includes a superior vena cava 18 and an aorta 20. Heart 16 pumps blood through aorta 20 into left subclavian artery 22, left carotid artery 24, right carotid artery 26, and right subclavian artery 28. Blood from the right subclavian artery 28 flows through a right axillary artery 30 and right brachial artery 32 into the radial and ulnar arteries 34, 36 to oxygenate the upper right extremity. Although not shown in FIG. 1, blood from heart 16 is similarly pumped through left subclavian artery 22 into a left axillary and left brachial artery (not shown).

Oxygenated blood is pumped from the left ventricle into the aorta through an aortic valve. The aortic valve comprises a cup shaped right coronary cusp 39 and a cup shaped left coronary cusp 41. Because of the orientation of the heart within the thorax 14, each of the cusps is slightly slanted with respect to a horizontal reference line.

The heart itself is oxygenated by blood pumped through the right coronary artery 38 and the left coronary artery 42. The right coronary artery 38 originates at an ostium 40, and the left coronary artery 42, originates at an ostium 44. Again because of the tilted orientation of heart 16 within thorax 14, the left ostium 44 is slightly higher than the right ostium 40. A great many heart diseases are caused by occlusion of arteries 38, 42, and it is therefore desirable to have a method by which the condition of these arteries can be determined.

The catheters shown in FIGS. 1-3 are designed for radiographic examination of arteries 38, 42. The catheter shown in FIG. 2 is configured for arteriography of the right coronary artery, and will be referred to by the reference numeral 46R. The catheter shown in FIG. 3 is configured for arteriography of a left coronary artery, and is referred to as catheter 46L. The common parts of both catheters 42R, 46L will be given common reference numerals, but will be differentiated by appending an R or L.

Each catheter 46 is comprised of an elongated tubular member of a conventional flexible catheter material, each member 48 having an interior channel therein which extends the length of the catheter 46. Each tubular member 48 is comprised of a shank 50 and an end part 52. The shank 50 has an enlarged collar member 54 at its origin, the interior diameter of collar member 54 being slightly greater than the interior diameter of tubular member 48. Each end part 52 is curved to provide a means for seating a portion of end part 52 against a wall of the aorta and another portion of end part 52 in a coronary cusp when the catheter is in place. This configuration of the catheter helps it stay in place throughout the procedure by fitting the catheter to the interior shape of aorta 20.

Right Coronary Catheter

With particular reference to the right coronary catheter 46R shown in FIG. 2, shank portion 50R is long enough to extend through the right brachial artery 32, right axillary artery 30, and right subclavian artery 28 into aorta 20. The shank portion at rest is substantially straight, but is made of a flexible material that can curve to the pathway defined by arteries 28, 30 and 32.

End portion 52R is substantially contained in a single plane and comprises, from shank portion 50R to a terminus 56 a first slightly curved portion 58, a second slightly curved portion 62 curving in a direction which is opposite the curvature of portion 58, and a generally J-shaped terminal portion 64.

The first slightly curved portion 58 curves in a first direction away from shank 50R to form a seating portion 66 for seating on a right side 60 of the interior wall of aorta 20 above ostium 40 of the right coronary artery 38. Curved portion 58 curves at an angle a of about 20° from a reference line $l_1$ through the straightened shank 50R.

Second slightly curved portion 62 is curved in a second direction which is opposite the direction of curvature of first curved portion 58. The curvature of second portion 62 forms a seating portion 68 for seating against a left side 70 of the interior wall of aorta 20 above the ostium 44 of left coronary artery 42. The degree of curvature of second portion 52 is illustrated, for example, by an angle b of about 20° and an angle c of about 20°, each of the angles b and c being taken with respect to a reference line $l_2$ parallel to shank 50R and which is tangent to seating portion 68.

The generally J-shaped terminal portion 64 includes a substantially straight segment 72, a strongly upwardly curved segment 74 and a slightly downwardly curved segment 76. The straight segment 72 is a continuation of curved segment 62 and is about 4 cm long, as measured from seating portion 68 to the beginning of the curvature of upwardly curved segment 74. Strongly upwardly curved segment 74 is about 1 cm long from the end of straight segment 72 to the beginning of downwardly curved segment 76. The strongly upwardly curved segment 74 is configured to seat in the right coronary cusp 39.

The slightly downwardly curved segment 76 is about 1.5 cm long and forms an angle d of about 50° with respect to a reference line $l_3$ through an ascending portion of segment 74.

Left Coronary Catheter

The left coronary catheter 46L in FIG. 3 comprises a shank portion 50L and end portion 52L. Shank portion 50L is long enough to extend through the right brachial artery 32 and right axillary artery 30, through right subclavian artery 28 and into aorta 20.

End portion 52L is substantially contained in one plane and is configured for seating securely in aorta 20. End portion 52L includes, from the shank to a terminus 78 of end portion 52L, a first slightly curved portion 80, and a generally U-shaped terminal portion. First portion 80 is curved to form a seating portion 84 for resting against a right side 60 of the interior wall of aorta 20 above the ostium 40 of right coronary artery 38. The U-shaped terminal portion is configured for seating in the left coronary cusp 41 below the ostium 44 of left coronary artery 42.

The U-shaped portion comprises, from shank 50 to terminus 78, a U-segment 86, a first inclined segment 88, and a second inclined segment 90. A descending leg 92 of U-segment 86 forms an angle e of about 30° with respect to a reference line $l_5$ through shank portion 50L. The descending leg 92 and an ascending leg 94 that completes the U have a combined length of about 30 cm as measured from point $p_1$ to point $p_2$.

First inclined segment 88 is about 1 cm long, and is inclined toward shank 50L at an angle f to reference line $l_6$, the line $l_6$ being parallel to line $l_5$ and tangent to the point $p_2$. Second inclined segment 90 is inclined at an angle G of about 45° defined between reference lines $l_7$, $l_8$, and is inclined away from shank 50L for seating in the ostium 44 of left coronary artery 42. Reference line $l_7$ is coincident with segment 88 and reference line $l_8$ is coincident with segment 90.

Method Of Operation

The catheter 50 can be used to perform a selective coronary arteriography of either the right or left coronary artery.

If an arteriography of the right coronary artery 38 is desired, the catheter 46R described above is used. Catheter 46R is inserted into right brachial artery 32 by inserting a flexible wire 55 into the artery through a needle, introducing a sheath over the wire, then introducing the catheter into the sheath. A pressure cuff is preferably placed around the upper arm during introduction of the needle, wire, sheath and catheter to reduce the surge of arterial blood pressure when the heart beats.

Collar member 54 at the end of shank portion 50R is coupled to a manifold 96 employed by injecting dye through the catheter. The flexible wire reinforcing member straightens end portion 52R to remove the curves. The straightened catheter is then advanced into the right brachial artery 32, through the right axillary artery 30 and right subclavian artery 28, into the aorta. Once the catheter is in place, the flexible member is removed from the channel and the plastic memory of catheter 46R returns portion 52R to the characteristic shape shown in FIGS. 1 and 2.

Catheter 46R is made of a radiopaque material, and can be positioned within aorta 20 by viewing its position on an X-ray screen. The catheter is manipulated until seating portion 66 is seated on right side 60 of the aorta, seating portion 68 is seated on the left side of the aorta, J-shaped terminal portion is seated within right coronary cusp 39, and downwardly curved segment 76 is seated in the ostium 40 of right coronary artery 38. The catheter can be easily placed in the position since its shape will conform to the shape of the aorta in which it is placed. Once catheter 46R is seated in this manner, it is firmly retained in position and cannot be easily dislodged until the procedure is finished. Radiopaque dye is introduced through line 99 into Tee 96, whence it then travels through catheter 46R and out an opening in terminus 56 into right coronary artery 38.

In case a coronary arteriography of the left coronary artery is to be performed, catheter 46L is used. The flexible wire member 55 is inserted into Artery 32 through a needle, a sheath is placed over the wire member 55, and catheter 46L is introduced into the sheath over wire member 55. Catheter 46L is then advanced through the right axillary artery 32 and right subclavian artery 30 into the aorta. The flexible wire member 55 is then removed from the channel, and the plastic memory of catheter 46L causes U-shaped terminal portion 82 to assume its characteristic shape shown in FIGS. 1 and 3. The catheter can be easily manipulated such that seating portion 84 is seated against the right side 60 of an interior wall of aorta 20, U-shaped segment 86 is seated in left coronary cusp 41, and second inclined segment 90 is seated in the ostium 44 of left coronary artery 42. Radiopaque dye is introduced through the catheter into the left coronary artery 42.

In the preferred embodiment of the invention, #5 French catheter is used. This type of catheter has a 2 mm. diameter (0.079" diameter).

Larger catheters are not preferably used from the arm, as they may cause injury to the brachial artery.

Having illustrated and described the principles of the invention in a preferred embodiment, it should be apparent to those skilled in the art that the invention can be modified without departing from such principles. This is particularly true with regard to the angles at which the segments of the catheter curve with respect to each other.

I claim all modifications coming within the spirit and scope of the following claims.

I claim:

1. A catheter for selective coronary arteriography of a coronary artery, the catheter comprising:
   an elongated, tubular member having an interior channel therein extending the length of the catheter, the catheter having a shank and an end part;
   the end part being curved to provide a means for seating a portion of said end part while resting against a wall of the aorta and for seating a portion of said end part in a coronary cusp while resting against the coronary cusp when the catheter is in place.

2. The catheter of claim 1 wherein the end part defines an opening through which a radiopaque material in introduced into the coronary artery, the end part having an upwardly curved terminal portion curving upwardly from the coronary cusp to a level adjacent an ostium of the coronary artery when the catheter is in place.

3. The catheter of claim 2 wherein the terminal portion comprises an upwardly curved segment which seats within the coronary cusp, and a downwardly curved segment which seats in the ostium.

4. The catheter of claim 1 wherein the catheter is a right coronary catheter, and the end part is substantially contained within one plane, the end part comprising, from the shank to a terminus of the end part:
   a first slightly curved portion curving in a first direction;
   a second slightly curved portion curving in a second direction which is opposite the first direction, for seating against the aortic wall; and
   a generally J-shaped terminal portion for seating in the right coronary cusp, the terminal portion having a length sufficient to extend upwardly to the ostium of the right coronary artery when the J is seated in the right coronary cusp.

5. The catheter of claim 4 wherein the terminal portion further comprises a downwardly curved segment for seating in the ostium of the right coronary artery, the downwardly curved segment defining a hole through which the radiopaque material can be introduced.

6. The catheter of claim 1 wherein the catheter is a left coronary catheter, and the end part is substantially contained within one plane, the end part comprising, from the shank to a terminus of the end part:
- a slightly curved first portion for seating against the aortic wall;
- a generally U-shaped terminal portion for seating in the left coronary cusp, the U-shaped portion having an ascending leg with a length sufficient to extend upwardly to the ostium of the left coronary artery.

7. The catheter of claim 6 wherein the terminal portion further comprises a slightly curved terminal segment which curves upwardly and away from the shank portion for seating in the ostium of the left coronary artery.

8. A right coronary catheter for coronary arteriography of a right coronary artery, the catheter comprising:
- an elongated, tubular member having an interior channel therein extending the length of the catheter, the catheter having a shank long enough to extend through a right brachial, right axillary and right subclavian artery to the aorta, and an end part for seating in the aorta;
- the end part being substantially contained in one plane and comprising from the shank to a terminus of the end part:
    - a first slightly curved portion curving in a first direction for seating on a right side of the interior wall of the aorta above the ostium of the right coronary artery;
    - a second slightly curved portion curving in a second direction which is opposite the first direction for seating against a left side of the interior wall of the aorta above the ostium of the left coronary artery, the curves of the first and second curved portions being substantially equal; and
    - a generally J-shaped terminal portion including a substantially straight segment about 4 cm long, a strongly upwardly curved segment about 1 cm long for seating in the right coronary cusp, and a slightly downwardly curved segment about 1.5 cm long for seating in the ostium of the right coronary artery.

9. A left coronary catheter for coronary arteriography of a left coronary artery, the catheter comprising:
- an elongated tubular member having an interior channel therein extending the length of the catheter, the catheter having a shank long enough to extend through a right brachial, right axillary and right subclavian artery to the aorta, and an end part for seating in the aorta;
- the end part being substantially contained in one plane and comprising, from the shank to a terminus of the end portion:
    - a slightly curved first portion for seating on a right side of the interior wall of the aorta above the ostium of the right coronary artery;
    - a generally U-shaped terminal portion for seating in the left coronary cusp and extending upwardly to the ostium of the left coronary artery, the terminal portion comprising, from the first portion to the terminus, a U-segment about 3 cm long, a first inclined segment about 1 cm long slightly curved toward the shank and a second inclined segment about 1.5 cm long slightly curved upwardly and away from the shank for seating in the ostium of the left coronary artery.

10. A method of selective coronary arteriography of a coronary artery, the method comprising the steps of:
- providing a catheter comprised of an elongated tubular member having an interior channel therein extending the length of the catheter, the catheter having a shank part and an end part, the end part being curved to provide a means for seating a portion of the end part while resting against a wall of the aorta and a portion of the end part while resting against a portion of a coronary cusp;
- providing placing a flexible, removable reinforcing member in the interior channel to straighten the end part while retaining its flexibility;
- inserting the reinforced catheter into a brachial artery and advancing the reinforced catheter through an axillary and subclavian artery to the aorta; and
- removing the reinforcing member and positioning the end part in the aorta with one of the curves of the end part seated against an interior wall of the aorta and another of the curves of the end part seated in a coronary cusp.

11. A method of selective coronary arteriography of a right coronary artery, the method comprising the steps of:
- providing a catheter comprised of an elongated, tubular member having an interior channel therein extending the length of the catheter, the catheter having a shank part long enough to extend through a right brachial, right axillary and right subclavian artery to the aorta, and an end part for seating in the aorta, the end part being substantially contained in one plane and comprising, from the shank to the terminus of the end part, one slightly curved portion curving in a first direction for seating on a right side of the interior wall of the aorta above the ostium of the right coronary artery, another slightly curved portion curving in a second direction which is opposite the first direction for seating against a left side of the interior wall of the aorta above the ostium of the left coronary artery, and a generally J-shaped terminal portion including a straight segment of about 4 1 cm length, a strongly upwardly curved segment about 1 cm long for seating against the right coronary cusp, and a slightly downwardly curved segment about 1.5 cm long for seating in the ostium of the right coronary artery;
- placing a flexible reinforcing member in the interior channel to straighten the end part while retaining its flexibility;
- inserting the reinforced catheter into a right brachial artery and advancing the reinforced catheter member through a right axillary and right subclavian artery to the aorta;
- removing the reinforcing member and positioning the end part in the aorta with one slightly curved portion seating on a right side wall of the interior wall of the aorta above the ostium of the right coronary artery, with another slightly curved portion seating against a left side of the interior wall of the aorta above the ostium of the left coronary artery, the strongly curved portion of the J-shaped terminal portion seating in the right coronary cusp, and the slightly downwardly curved segment seating in the ostium of the right coronary artery.

12. A method of selective coronary arteriography of a left coronary artery, the method comprising the steps of:

providing a catheter comprised of an elongated tubular member having an interior channel therein extending the length of the catheter, the catheter having a shank part long enough to extend through a right brachial, right axillary and right subclavian artery to the aorta, and an end part for seating in the aorta, the end part being substantially contained in one plane and comprising, from the shank to the terminus of the end part, a slightly curved first portion for seating against a right side of the aortic wall above the ostium of the right coronary artery, and a generally U-shaped terminal portion for seating in the left coronary cusp and extending upwardly to the ostium of the left coronary artery, the terminal portion comprising, from the shank to the terminus, a U-segment about 3 cm long, a first inclined segment about 1 cm long slightly curved in the direction of the shank, and a second inclined segment about 1.5 cm long slightly curved upwardly and away from the shank;

providing placing a flexible reinforcing member in the interior channel to straighten the end part while retaining its flexibility;

inserting the reinforced catheter into a right brachial artery and advancing the catheter through a right axillary and right subclavian artery to the aorta; and removing the reinforcing member and positioning the end part in the aorta with the curved first portion seated against a right wall of the aorta above the ostium of the right coronary artery, the U-segment seated in the left coronary cusp, and the second inclined segment seated in the ostium of the left coronary artery.

* * * * *